(12) United States Patent
Colosimo et al.

(10) Patent No.: US 9,465,061 B2
(45) Date of Patent: Oct. 11, 2016

(54) IN-PROCESS MATERIAL CHARACTERIZATION

(71) Applicant: TransTech Systems, Inc., Schenectady, NY (US)

(72) Inventors: Donald D. Colosimo, Saratoga Springs, NY (US); Sarah E. Pluta, Scotia, NY (US)

(73) Assignee: TransTech Systems, Inc., Schenectady, NY (US)

( * ) Notice: Subject to any disclaimer, the term of this patent is extended or adjusted under 35 U.S.C. 154(b) by 769 days.

(21) Appl. No.: 13/893,398

(22) Filed: May 14, 2013

(65) Prior Publication Data

US 2013/0307564 A1 Nov. 21, 2013

Related U.S. Application Data

(60) Provisional application No. 61/647,848, filed on May 16, 2012.

(51) Int. Cl.
| | | |
|---|---|---|
| *G01R 27/32* | (2006.01) | |
| *G01R 27/06* | (2006.01) | |
| *G01N 22/00* | (2006.01) | |

(52) U.S. Cl.
CPC ............ *G01R 27/06* (2013.01); *G01N 22/00* (2013.01)

(58) Field of Classification Search
CPC ............ G01N 35/1065; G01N 21/84; G01R 31/2637; G01R 31/2837; G01V 3/17
USPC .......... 324/500, 600, 637–661, 76.11, 76.26, 324/444, 447, 515, 559
See application file for complete search history.

(56) References Cited

U.S. PATENT DOCUMENTS

| | | |
|---|---|---|
| 2,240,520 A | 5/1941 | Schlumberger |
| 2,264,725 A | 12/1941 | Shoupp et al. |
| 4,979,197 A | 12/1990 | Troxler, Sr. et al. |
| 5,099,504 A | 3/1992 | Pettit |
| 5,272,624 A | 12/1993 | Gisser et al. |
| 5,381,333 A | 1/1995 | Isaacson et al. |
| 5,544,662 A | 8/1996 | Saulnier et al. |

(Continued)

FOREIGN PATENT DOCUMENTS

WO  2010144313 A2  12/2010

OTHER PUBLICATIONS

Dahlin, T., et. al. "Combined Resistivity Imaging and RCPT for Geotechnical Pre-investigation", Procs. NGM 2004, Ystad, Sweden.

(Continued)

*Primary Examiner* — Melissa Koval
*Assistant Examiner* — Trung Nguyen
(74) *Attorney, Agent, or Firm* — Hoffman Warnick LLC (57) ABSTRACT

Various embodiments include solutions for in-process material characterization. Various particular embodiments include a computer-implemented method including: providing instructions for transmitting oscillating electromagnetic field signals to a material under test (MUT); obtaining a return signal associated with the transmitted oscillating electromagnetic field signals; comparing the return signal with the oscillating electromagnetic field signals to determine a difference in an aspect of the return signal and the aspect of the oscillating electromagnetic field signals; comparing the difference in the aspect to a predetermined threshold; and determining a characteristic of the MUT based upon the compared difference.

15 Claims, 10 Drawing Sheets

(56) References Cited

U.S. PATENT DOCUMENTS

| | | | |
|---|---|---|---|
| 5,890,489 | A | 4/1999 | Elden |
| 5,900,736 | A | 5/1999 | Sovik et al. |
| 6,380,745 | B1 | 4/2002 | Anderson et al. |
| 6,414,497 | B1 | 7/2002 | Sovik et al. |
| 6,703,847 | B2 | 3/2004 | Venter et al. |
| 7,040,145 | B2 | 5/2006 | Drnevich et al. |
| 7,068,050 | B2 | 6/2006 | Steele et al. |
| 7,219,024 | B2 | 5/2007 | Gamache et al. |
| 7,701,227 | B2 | 4/2010 | Saulnier et al. |
| 8,011,248 | B2 | 9/2011 | Troxler |
| 2002/0032531 | A1* | 3/2002 | Mansky ............... B01J 19/0046 702/21 |
| 2005/0267700 | A1* | 12/2005 | Gamache ............ G01N 27/028 702/65 |
| 2009/0270756 | A1 | 10/2009 | Gamache et al. |

OTHER PUBLICATIONS

Kulkarni, R., Boverman, G., Isaacson, D., Saulnier, G. J., Kao, T., Newell, J. (2008) An Analytical Layered Forward Model for Breasts in Electrical Impedance Tomography. Physiol Meas. 29(6): S27-S40.

Kulkarni, R., Kao, T., Boverman, G., Isaacson, D., Saulnier, G. J., Newell, J. (2009) A Two-Layered Forward Model of Tissue for Electrical Impedance Tomography. Physiol Meas. 30(6): S19-S34.

Sandia National Laboratories, "Hybrid Hydrologic-Geophysical Inverse Technique for Assessment and Monitoring in the Vadose Zone", SNL Report.

Belge, M., Kilmer, M. and Miller, Eric L., "Wavelet Domain Image Restoration with Adaptive Edge-Preserving Regularization," IEEE Trans. on Image Processing, vol. 9, No. 4, Apr. 2000, pp. 597-608.

Charbonnier P, Blanc-Féraud L, Aubert G, Barlaud M. Deterministic edge-preserving regularization in computed imaging. IEEE Transactions on Image Processing 1997;6(2):298-311.

Cornean, Horia; Knudsen, K. and Siltanen, S., "Towards a d-bar reconstruction method for three-dimensional EIT", Version 8, submitted Mar. 2005.

El-Shenawee, Magda and Miller, Eric L., "Spherical Harmonics Wideband Polarimetric Algorithm for Shape and Location Reconstruction of Three-Dimensional Malignant Breast Cancer Tumor," IEEE Transactions on Medical Imaging, vol. 25, No. 10, Oct. 2006, pp. 1258-1271.

Gamache, R. W. (2004). "FEA software ready to model many physical phenomena", Machine Design, Jul. 8, 2004, 132-135.

Gamache, R., "Electromagnetic Material Properties Sensor", COMSOL Multiphysics Conference, Boston, MA 2005.

Gamache, R., Rappaport, C. and Farid, A., "A Comparison of FDFD and FEM Methods Applied to the Buried Mine Problem", COMSOL Multiphysics Conference, Boston, MA 2006.

Hilhorst, M. A. (1998), "Dielectric Characterization of Soil," Wageningen, Netherlands.

Loke, M., "A practical guide to 2-D and 3-D surveys", Penang, Malaysia, 1999.

Neithalath N, Weiss J , Olek J. (2006). Characterizing Enhanced Porosity Concrete Using Electrical Impedance to Predict Acoustic and Hydraulic Performance. Cement and Concrete Research vol. 36, Issue 11, Nov. 2006, pp. 2074-2085.

Nyfors, E.; Vainikainen, P. (1991) Industrial microwave sensors. Microwave Symposium Digest, 1991., IEEE MTT-S International.

Roth, K., Schulin, R., Fluhler, H., and Attinger, W., "Calibration of Time Domain Reflectometry for Water Content Measurement Using a Composite Dielectric Approach," Water Resources Research, 26(10): 2267-2273, 1990.

Schlumberger, C., M. Schlumberger (1932) Depth of Investigation Attainable by Potential methods of Electrical Exploration. Aime Trans. Geophys. Prosp., 97: 127-133.

Xiong Yu, Vincent P. Drnevich, Jan Olek (2004) Time Domain Reflectometry for Measuring Water cement Ratio of Concrete. International RILEM Symposium on Concrete Science and Engineering: A Tribute to Arnon Bentur RILEM Publications SARL 2004 e-ISBN: 2912143926.

\* cited by examiner

IN-PROCESS MATERIAL CHARACTERIZATION

CROSS REFERENCE TO RELATED APPLICATIONS

This application claims the benefit of U.S. Provisional Application Ser. No. 61/647,848, filed on May 16, 2012, which is incorporated by reference herein in its entirety.

TECHNICAL FIELD

The invention relates to characterizing material properties of items. More particularly, the invention relates to characterizing of material properties of items, e.g., during the production process

BACKGROUND

Quality control and quality assurance during manufacturing processes are important objectives for industry. The inspection of the manufactured item may occur non-destructively or destructively, in-process or off-line. Inspecting one or more manufactured items can cause a number of concerns, which prior approaches fail to adequately address.

SUMMARY OF THE INVENTION

Aspects of the invention include systems and methods for performing non-destructive, in-process inspection of specified layers/volumes of material properties of a product, e.g., during or proximate in time to a manufacturing process.

Various embodiments include a system having: an array of electrodes for non-conductively communicating with a material under test (MUT); a signal generator operably connected with the array of electrodes, the signal generator for transmitting oscillating electromagnetic field signals from the array of electrodes at a range of frequencies; and at least one computing device operably connected with the signal generator and the array of electrodes, the at least one computing device configured to: obtain a return signal from the array of electrodes about the MUT; compare the return signal with the oscillating electromagnetic field signals to determine a difference in an aspect of the return signal and the aspect of the oscillating electromagnetic field signals; compare the difference in the aspect to a predetermined threshold; and determine a characteristic of the MUT based upon the compared difference.

Various other embodiments include a computer program having program code stored on a computer-readable medium, which when executed by at least one computing device, causes the at least one computing device to: provide instructions for transmitting oscillating electromagnetic field signals to a material under test (MUT); obtain a return signal associated with the transmitted oscillating electromagnetic field signals; compare the return signal with the oscillating electromagnetic field signals to determine a difference in an aspect of the return signal and the aspect of the oscillating electromagnetic field signals; compare the difference in the aspect to a predetermined threshold; and determine a characteristic of the MUT based upon the compared difference.

Various additional embodiments include a computer-implemented method including: providing instructions for transmitting oscillating electromagnetic field signals to a material under test (MUT); obtaining a return signal associated with the transmitted oscillating electromagnetic field signals; comparing the return signal with the oscillating electromagnetic field signals to determine a difference in an aspect of the return signal and the aspect of the oscillating electromagnetic field signals; comparing the difference in the aspect to a predetermined threshold; and determining a characteristic of the MUT based upon the compared difference.

DETAILED DESCRIPTION

As noted herein, various aspects of the invention include systems and methods for performing non-destructive, in-process inspection of specified layers/volumes of material properties of a product, e.g., during or proximate in time to a manufacturing process.

Various embodiments include a system having: an array of electrodes for non-conductively communicating with a material under test (MUT); a signal generator operably connected with the array of electrodes, the signal generator for transmitting oscillating electromagnetic field signals from the array of electrodes at a range of frequencies; and at least one computing device operably connected with the signal generator and the array of electrodes, the at least one computing device configured to: obtain a return signal from the array of electrodes about the MUT; compare the return signal with the oscillating electromagnetic field signals to determine a difference in an aspect of the return signal and the aspect of the oscillating electromagnetic field signals; compare the difference in the aspect to a predetermined threshold; and determine a characteristic of the MUT based upon the compared difference.

Various other embodiments include a computer program having program code stored on a computer-readable medium, which when executed by at least one computing device, causes the at least one computing device to: provide instructions for transmitting oscillating electromagnetic field signals to a material under test (MUT); obtain a return signal associated with the transmitted oscillating electromagnetic field signals; compare the return signal with the oscillating electromagnetic field signals to determine a difference in an aspect of the return signal and the aspect of the oscillating electromagnetic field signals; compare the difference in the aspect to a predetermined threshold; and determine a characteristic of the MUT based upon the compared difference.

Various additional embodiments include a computer-implemented method including: providing instructions for transmitting oscillating electromagnetic field signals to a material under test (MUT); obtaining a return signal associated with the transmitted oscillating electromagnetic field signals; comparing the return signal with the oscillating electromagnetic field signals to determine a difference in an aspect of the return signal and the aspect of the oscillating electromagnetic field signals; comparing the difference in the aspect to a predetermined threshold; and determining a characteristic of the MUT based upon the compared difference.

As described herein, the objective of non-conductively determining characteristics of a MUT can be achieved by the application of impedance spectrographic tomography. The application of impedance spectrographic tomography is based on the use of a sensor array which is not in conductive electrical contact with the MUT, and the application of an electromagnetic field over a range of frequencies selected to enhance (and in some cases, optimize) the identification of the features of the material under test.

The sensor array can be designed to provide readings of different layers/volumes of the material under test. The measured complex impedance from the various layers of the material can then be analyzed by various methods to produce a complex impedance value for each of the various layers under examination. These values of complex impedance may then be used to correlate with desired properties of the material under test, either as a qualitative control or as a quantitative control for a physical property measurement, which can be related to the measured complex impedance through a conversion algorithm. The resulting correlation to a physical property of the material can then be used for manufacturing process control. This may range from a manual process or a fully integrated Statistical Process Control (SPC) system to determine variations in the manufacturing process. Whichever manufacturing method is used, the information would then be used to control the manufacturing process.

In achieving this objective, the shortcomings of conventional methodologies are overcome. Specifically, some of the conventional methodologies require that there be direct electrical contact with the material under test. None of the conventional methodologies provide information about specified layers/volumes of the MUT. Additionally, all of the nuclear based conventional methodologies employ radioactive materials which pose environmental and national security risks. As noted herein, various embodiments of the invention overcome the limitations of the conventional approaches.

Quality control and quality assurance during manufacturing processes can be important objectives for industry. The inspection of a manufactured item may occur non-destructively or destructively, in-process or off-line. Inspecting one or more manufactured items can cause a number of concerns, which conventional approaches fail to adequately address.

A desirable method of examining a material is non-destructively and in-process. These measurements combined with various monitoring methodologies, such Statistical Process Control (SPC), with production control feedback enhances the assurance that the product is being manufactured within specifications and minimizes the cost of scrapped product. There are various technologies that are conventionally used to accomplish this objective. Some of these are not applicable to some materials and others, such as those with a nuclear radioactive source, present an environmental or national security problem.

Currently, the methods used in some industrial processes for the inspections of products that involve the determination of density and/or moisture require destructive techniques. For example, the product is removed from the production line and measurements are made that involve the destruction of the product. Aside from the removal of product, these inspection processes are not performed in real-time and, by necessity, result in the inspection of very small number of samples. In the following discussion(s), the production of concrete blocks is used as an example. This does not limit the scope of the application of the subject matter.

Impedance Spectroscopy Background:

Impedance spectroscopy has been used for the evaluation of material characteristics. In general, the macroscopic interaction of electromagnetic fields with materials is described by Maxwell's equations. Solution of Maxwell's equations involves knowledge of three constitutive properties of the material: the magnetic permeability, the dielectric permittivity, and the electrical conductivity. In general, these parameters are dependent upon material composition and physical properties, temperature, and frequency of the applied field.

Figure 1:
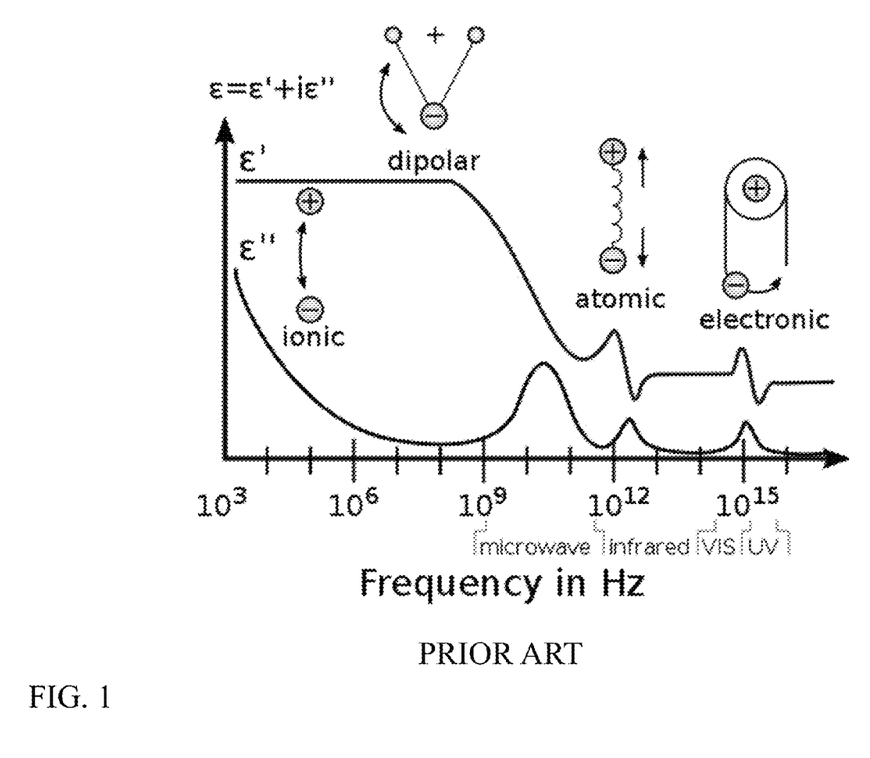
FIG. 1 is an illustration of the dielectric spectrum of an idealized material according to the prior art.

As opposed to the response of a vacuum, the response of normal materials to external fields generally depends on the frequency of the field (FIG. 1). This frequency spectroscopy is due to the fact that a material's polarization does not respond instantaneously to an applied field. The response must always be causal (arising after the applied field) which can be represented by a phase difference. For this reason permittivity is often treated as a complex function (since complex numbers allow specification of magnitude and phase) of the (angular) frequency of the applied field ω, $\in \rightarrow \hat{\in}(\omega)$. The definition of permittivity therefore becomes:

$$D_0 e^{-i\omega t} = \hat{\in}(\omega) E_0 e^{-i\omega t}, \quad \text{(Equation 1)}$$

where $D_0$ and $E_0$ are the amplitudes of the displacement and electrical fields, respectively, i is the imaginary unit, $i^2 = -1$.

The response of a medium to static electric fields is described by the low-frequency limit of permittivity, also called the static permittivity $\in_s$ (also $\in_{DC}$):

$$\varepsilon_s = \lim_{\omega \to 0} \hat{\varepsilon}(\omega). \quad \text{(Equation 2)}$$

At the high-frequency limit, the complex permittivity is commonly referred to as $\in_\infty$. At the plasma frequency and above, dielectrics behave as ideal metals, with electron gas behavior. The static permittivity is a good approximation for alternating fields of low frequencies, and as the frequency increases a measurable phase difference δ emerges between D and E. The frequency at which the phase shift becomes noticeable depends on temperature and the details of the medium. For moderate field strength ($E_0$), D and E remain proportional, and:

$$\hat{\varepsilon} = \frac{D_0}{E_0} = |\varepsilon| e^{i\delta}. \quad \text{(Equation 3)}$$

Since the response of materials to alternating fields is characterized by a complex permittivity, it is natural to separate its real and imaginary parts, which is done by convention in the following way:

$$\hat{\varepsilon}(\omega) = \varepsilon'(\omega) + i\varepsilon''(\omega) = \frac{D_0}{E_0}(\cos\delta + i\sin\delta). \quad \text{(Equation 4)}$$

Where:

$\in''$ is the imaginary part of the permittivity, which is related to the dissipation (or loss) of energy within the medium; and $-\in'$ is the real part of the permittivity, which is related to the stored energy within the medium.

It may be helpful to realize that the choice of sign for time-dependence, exp (−iωt), dictates the sign convention for the imaginary part of permittivity. The signs used here correspond to those commonly used in physics, whereas for the engineering convention one should reverse all imaginary quantities.

The complex permittivity is usually a complicated function of frequency w, since it is a superimposed description of dispersion phenomena occurring at multiple frequencies. The dielectric function $\in(\omega)$ must have poles only for frequencies with positive imaginary parts. However, in the narrow frequency ranges that are often studied in practice, the permittivity can be approximated as frequency-independent or by model functions.

In the following discussion, application of electromagnetic fields to soils and concrete will be discussed to illustrate the effects of making measurements on actual materials. Soils share an important characteristic with concrete and the other materials to which this technology can be applied in that they all contain water. The determination of a material characteristic where the material contains water is a difficult problem. Typically, for the materials of interest described herein, as well as many soils, the permeability is nearly that of free space and the conductivity is low (2-6 mS/cm). As a result, the electromagnetic response of soil is primarily determined by its dielectric properties. Soil can be a porous medium consisting of a heterogeneous mixture of pore fluids, air and soil particles of different minerology, size, shape and orientation.

Figure 2:
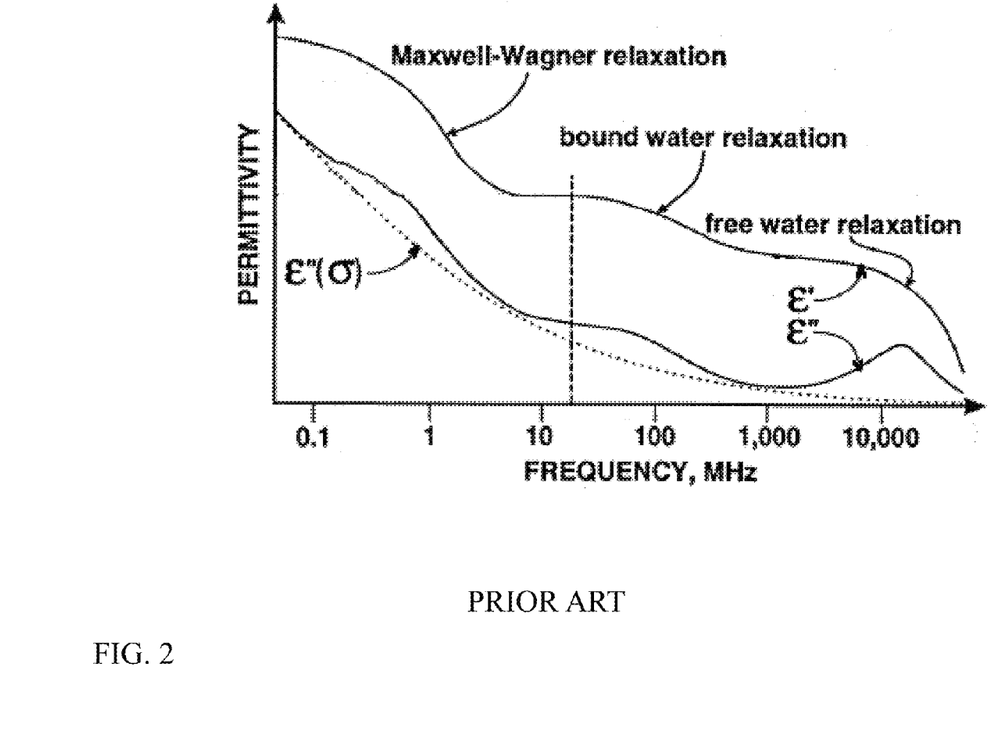
FIG. 2 is an illustration of the dielectric spectrum of a real material, soil, after a soil analysis according to the prior art.

The heterogeneity of soil combined with significant interfacial effects between the highly polar water molecules and the soil solids surface results in a complex electrical response for which good conventional phenomenological theories do not exist. There are three primary polarization effects in soil: bound water polarization, double layer polarization, and the Maxwell-Wagner (M-W) effect (FIG. 2). The bound water polarization results from the fact that water can be electrostatically bound to the soil matrix. The degree of binding varies from unbound or free water at a great distance (>10 molecular diameters) from the matrix surface, to heavily bound, or adsorbed, water.

If water becomes bound to the soil matrix, it may not be capable of doing as much work, and hence has lost energy. The relaxation frequency and the apparent dielectric constant of bound water are significantly less than that of free water. Double layer polarization is due to separation of cations and anions in an electric double layer around plate-like clay particles. It is a surface phenomenon that is dominant at frequencies <100 kHz. Double layer polarization is mostly observed in soils containing a large fraction of clay. The M-W effect is one of the most important phenomena which affects the low radio frequency dielectric spectrum of soils. The M-W effect is a macroscopic phenomenon that depends on the differences in dielectric properties of the soil constituents. It is a result of the distribution of conducting and non-conducting areas in the soil matrix. This interfacial effect is dominant at frequencies between 100 kilo-Hertz (kHz) and 20 mega-Hertz (MHz), below the frequencies where bound and free water relaxations plays a dominant role. Above this frequency range, the dielectric response can be empirically described by mixing equations in which the matrix bulk dielectric constant is proportional to the sum of the products of the volume fractions and dielectric constants of the constituents. At frequencies below the M-W relaxation, the apparent permittivity may increase more than an order of magnitude from its value in the mixing region. The conductivity is also dispersive, falling with frequency, as shown in FIG. 2. The dielectric spectrum can be roughly divided into two parts. The higher frequencies can be dominated by the bound and free water relaxations and the lower frequencies are dominated by the M-W effect.

The dielectric characterisitics of soils may be considered as a mixture of essentially three components: air, stone, and water, with water acting to help bind the stone matrix together. Some researchers have shown that the matrix bulk dielectric constant may be derived from the volume fractions and dielectric constants of the constituents according to the following, empirically derived, soil dielectric mixing equation:

$$k = [\theta k_w^\alpha (1-\eta) k_s^\alpha + (\eta-\theta) k_a^\alpha]^{1/\alpha} \quad \text{(Equation 5)}$$

Here, k is the bulk dielectric constant; $k_w$, $k_s$, $k_a$ are the respective dielectric constants of water, stone, and air; θ is the volume fraction of water; η is the porosity (so that 1−η is the volume fraction of stone, and η−θ is the volume fraction of air); and α is an empirically determined constant, different for each soil matrix. For sandy type soil matrices, α=0.46 has been found to be typical. Typical values for the component permittivity are: $k_s$=3-5, $k_w$=80, and $k_a$=1. As compaction increases, porosity decreases; the $k_s$ term drives k upward, while the $k_a$ term drives k downward, but because $k_s > k_a$, the net effect is an increase in k (regardless of the value of α, and even if α<0). The mathematics confirms: when you squeeze out the component with the lowest dielectric constant, the bulk dielectric constant should increase. The changes due to the reduction of the air in the mix and the relaxation characteristics of water are used in impedance spectroscopy to determine the density and moisture content of the soil.

In materials with bound and/or free water, the M-W effect may be used to aid in the determination of the characteristic of the material. This is also true of concrete where the water is undergoing a chemical bounding termed hydration, which is the chemical reaction:

$$2Ca_3SiO_5 + 7H_2O \rightarrow 3(CaO).2(SiO_2).4(H_2O)(gel) + 3Ca(OH)_2 \quad \text{(Equation 6)}$$

A number of authors have investigated the dielectric and impedance responses of concrete. In these studies, it was shown that changes in amount of water in the concrete mix and the stages of hydration affect the resultant complex impedance.

Materials that contain polar components, like water, may also produce relaxations which may be used in characterizing the state of the material under test. For materials that do not contain water or other polar components, it is expected that there are other characteristics which will produce changes in the impedance spectrographic signal. For example, asphalt is a material which contains virtually negligible amounts of water. Asphalt, too, is a mixture of essentially three components: air, stone, and bituminous binder. A corresponding asphalt dielectric mixing equation would be:

$$k = [\upsilon k_b^\alpha + (1-\eta)k_s^\alpha + (\eta-\upsilon)k_a^\alpha]^{1/\alpha}$$ (Equation 7)

with $\upsilon$ and $k_b$, representing respectively, the volume fraction and dielectric constant of the bituminous binder. The mixture is precisely controlled and heated to over 350° F. during production and is laid down at a temperature of approximately 300° F.

Impedance Tomography Background:

Impedance tomography has been used in a number of conventional research and development programs. Some of the techniques have been and are being applied to other tomographic modalities, such as Magnetic Resonance Imaging (MRI), Computed Assisted Tomography (CAT), and others. A list of some of the many different approaches that can be used to develop an "image" from tomographic signals is presented below. While these approaches can provide an adequate 2-D or 3-D image, they require extensive data and/or extensive computation. Approaches followed according to various examples herein, as discussed further below, can be based on a layered method.

Electromagnetic Inversion Methods Background:

Typical electromagnetic inverse-type methods begin by discretizing the region of interest into a large collection of voxels over which complex permittivity is assumed constant.

Electrical Resistance Tomography:

Electrical resistance tomography is based on the injection of electrical current into the earth at one location and the measurement of the resulting voltage drop across a pair of electrodes located elsewhere. By varying the locations of the current source and measurement electrodes using multiple boreholes or surface measurements and exploiting the physics relating the input current, output voltages, and electrical properties of the earth, it is possible to process the data to develop an "image" of the electrical conductivity in the region bounded by the measurement apparatus.

Shape Based Methods:

Over the past two decades, the image processing and computer vision communities have developed a range of methods for modeling shapes in 2D and 3D scenes. These methods basically function by aggregating pixels (or "voxels") in a scene into those that are "inside" and those that are "outside" a region of interest.

Layered Forward Model:

This approach was developed to handle the problem posed by the inhomogeneous structure of human tissue, with thin low admittivity skin layers covering the relatively high admittivity tissue inside, making the imaging problem difficult. In addition, studies show that the electrical properties of skin vary considerably over frequency. The layered forward model incorporates the presence of skin. One layered model has three layers, thin low admittivity top and bottom layers representing skin and a thicker high admittivity middle layer representing tissue.

Applicants' Approach:

For the purpose of promoting an understanding of the principals of the invention, reference will now be made to the embodiments as illustrated in the drawings and specific language will be used to describe the same. It will nevertheless be understood that no limitation of the scope of the invention is thereby intended, such alterations and further modifications in the illustrated device and such further applications of the principal of the invention as illustrated therein being contemplated as would normally occur to one skilled in the art to which the invention relates.

Figure 3:
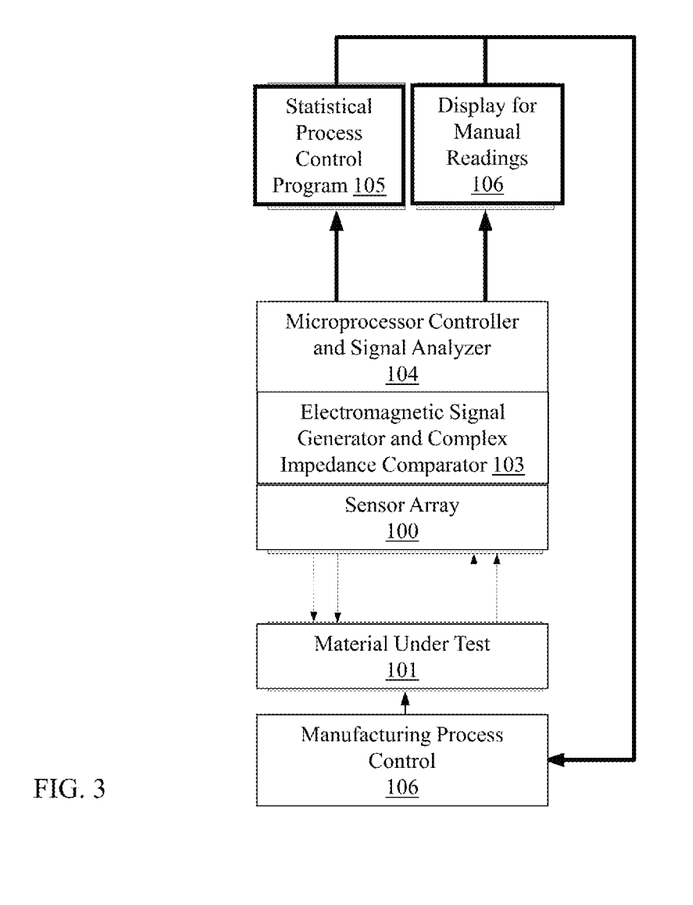
FIG. 3 is a block diagram of the process of the application of the invention.

The basic approach to the system design is shown in FIG. 3. As we move toward making measurements and interpreting aspects of the complex impedance, it can be helpful to define terms that may be calculated from the output of the measurement device which are the magnitude of the power of the signal that is transmitted through the MUT, m, and the phase angle, δ, shift between the transmitted signal and which occurs as the signal passes through the MUT. Impedance (Z) is represented mathematically as a complex relation consisting of a real part, Resistance, and an imaginary part, Reactance:

$$Z = R + iX;$$

Z=the complex value of Impedance;
R=the Resistance;
X=the Reactance.

Resistance, R, is a material's opposition to the flow of electric current.

Reactance, X, is a material's opposition to alternating current due to capacitance (capacitive reactance) and/or inductance (inductive reactance).

Susceptance (B) is a complementary representation of the Reactance in the term Admittance and is defined mathematically as:

$$B = -X^2/(R^2+X^2)$$

B=the Susceptance=m*sin δ.

Admittance (Y) is a complex quantity which is the inverse of Impedance, and results in the definition of the terms of Conductance and Susceptance:

$$Y = 1/Z = G + iB;$$

Y=the Admittance;
G=the Conductance=m*cos δ.

The sensor array can interact with the material under test to obtain the complex impedance over a range of frequencies selected to enhance (e.g., maximize) the sensitivity to the properties of interest. In various embodiments, the range of frequencies can span between approximately 1 kHz and approximately 50 MHz. The particular range of frequencies can be based upon material properties of the MUT (e.g., a dielectric constant of the MUT) and/or a desired depth of penetration into the MUT. In a particular example, the range of frequencies applied to a wet (at least partially saturated) concrete is approximately 10 kHz to approximately 5 MHz.

The resultant values of the complex impedance in terms of the magnitude change and the phase shift of the signal passing through the material under test relative to the input signal is processed by the microprocessor. The signal may consist of an algorithm of the complex impedance such as a function of the susceptance or conductance over a range of frequencies or an empirical correlation of the complex impedance to one or more physical properties of the material. This result can be transmitted either to display for manual data entry or to a statistical process control program.

The manual evaluation is able to result in a pass-fail result or the data may be entered into some type of statistical analysis for further processing and evaluation. A statistical process control program determines if the sample meets the required quality within a specified statistical limit. Whichever method is used, the result is then passed to the manufacturing process control for action.

Figure 4:
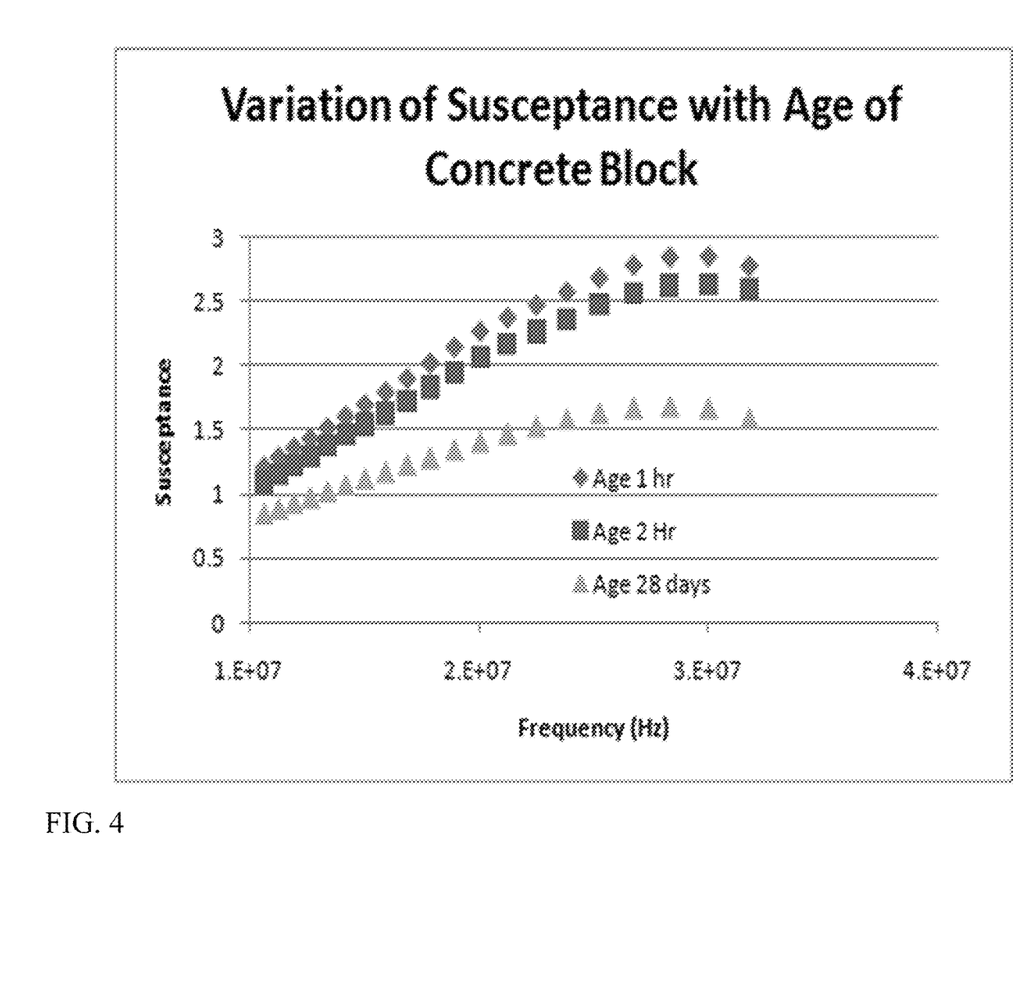
FIG. 4 is the presentation of the complex impedance of concrete blocks showing the variation of susceptance with the age of the blocks, illustrating the changes in one aspect of the complex impedance spectrum.

FIG. 4 shows an example of the variation of the one aspect of the complex impedance spectrum, in this case the susceptance (B), due to the aging of a concrete block during production.

Figure 5:
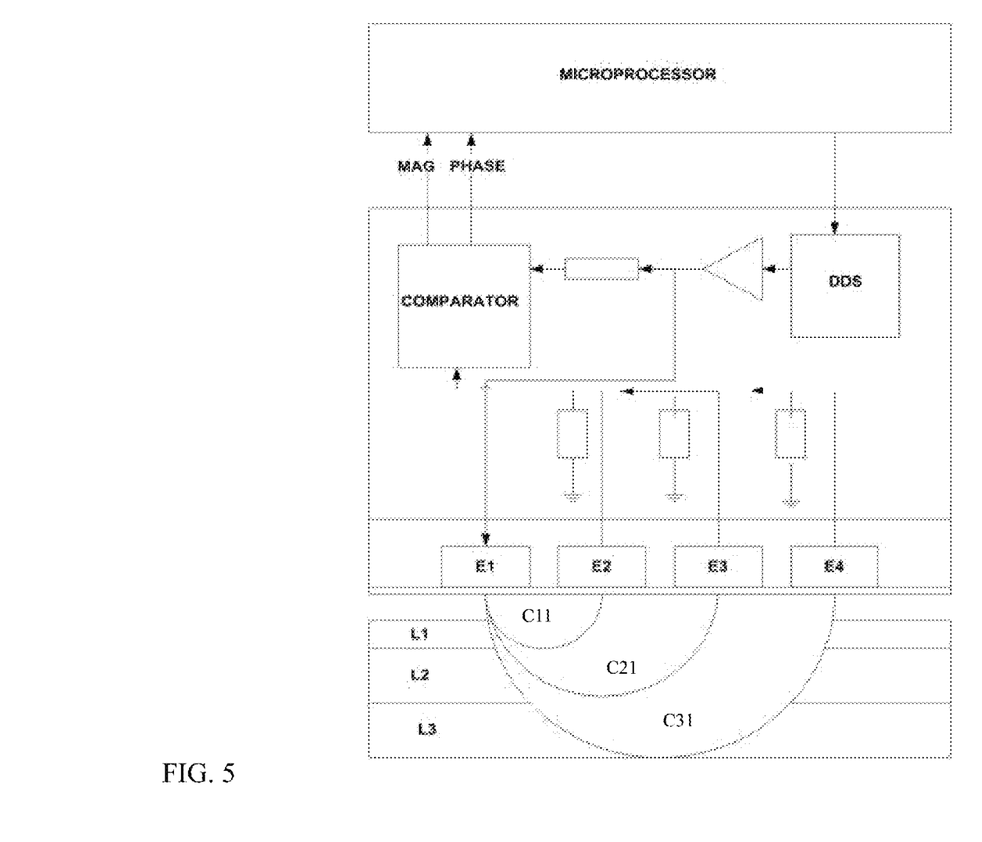
FIG. 5 is a schematic of the invention interacting with a material under test.

A more detailed schematic of the invention is shown in FIG. 5. This shows that the sensor system can include four electrodes, one of which provides the input of the signal over a range of frequencies supplied by a signal generator, e.g., a DDS (Direct Digital Synthesizer). In this example, the other three electrodes complete the circuit with the signal passing through the material under test. The original signal from the DDS is compared to the signals passing through the material under test. The output of the comparator is the difference in the magnitude of the signals and the phase shift. This magnitude and phase data is transmitted to the microprocessor which processes the data and transmits it to the statistical process control. The microprocessor also controls the DDS to select the frequencies to be generated. Also shown is the material under test with three layers/volumes of interest. This is explained further herein.

As noted herein, the electrodes are configured to communicate with the material under test (MUT) but are not in electrical contact with the MUT, that is, they are electrically isolated from the MUT. In some cases, the minimum number of electrodes in the array is three (3), which may be a minimum number in order to determine the properties of two layers/volumes in the MUT.

Figure 6:
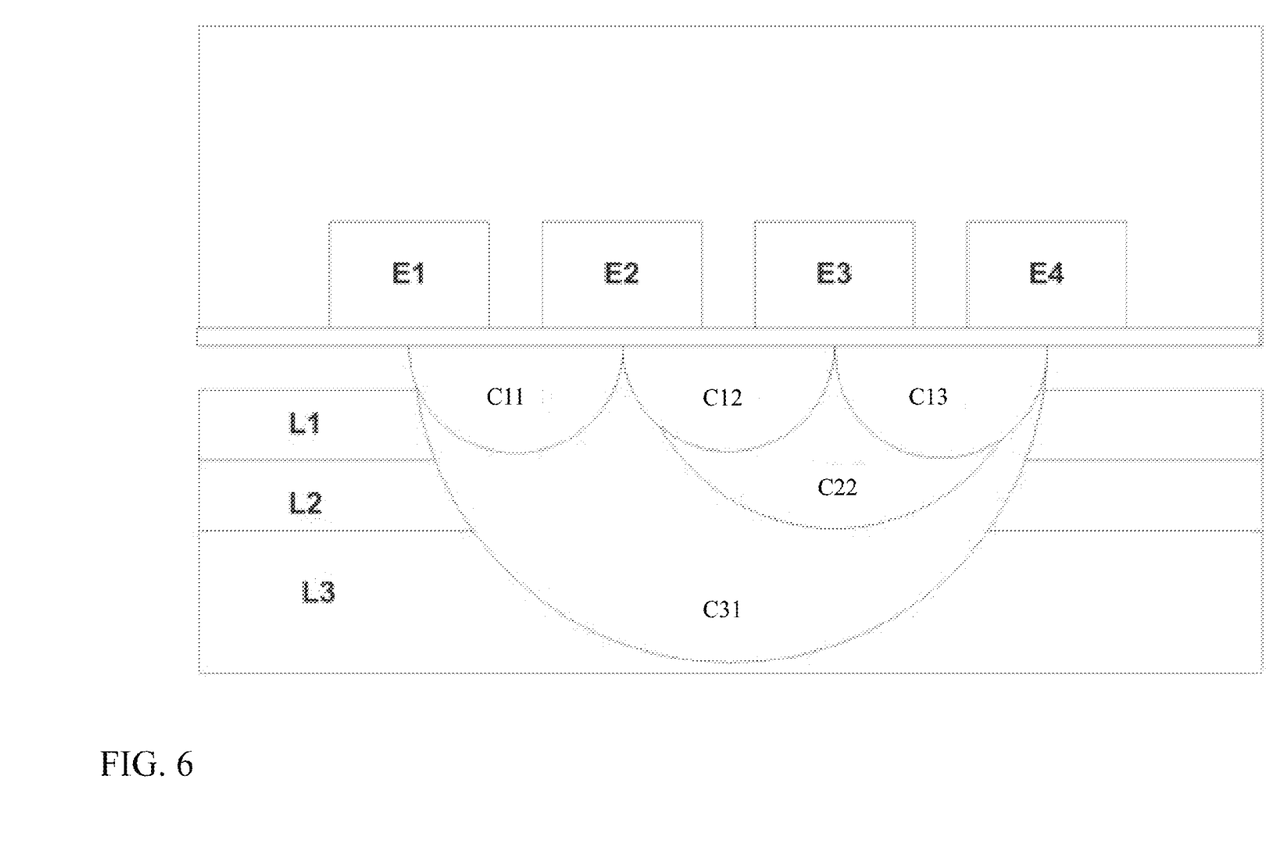
FIG. 6 is an illustration of the measurement of the complex impedance of various layers/volumes.

FIG. 6 presents a starting point for the sensor design. This design has a total of four electrodes, arranged in a linear array, which are capable of sensing at least three different layers/volumes. The electrodes are electrically insulated from the test material and may be in contact with the MUT in some cases, and may be physically separated from the MUT in other cases. In some embodiments, the electrodes are separated from the MUT by an air gap. The air gap can electrically insulate the electrodes from the MUT, as well as physically separate the electrodes from the MUT. In some particular embodiments, the air gap is less than approximately 0.25 inches wide.

Each of the electrodes may be either a transmitter or a receiver in order to provide the measurements at different depths and the measurements for the tomographic evaluations of the three layers. The tomographic approach is discussed further herein.

The electrodes may be arranged in any number of manners, and may be arranged in a planar array. In some cases, the planar array can include a linear array of electrodes. In other cases, the planar array includes a two-dimensional array of electrodes.

In various embodiments, the electrodes can be spaced apart in such a manner as to obtain a desired amount of depth penetration into the MUT. For example, generally, the electrodes may be spaced apart in such a manner that for penetration to a desired depth X, the electrodes are spaced apart a distance of 2x. That is, in various embodiments, each electrode is spaced apart from its adjacent electrode at twice the distance of the desired penetration into the MUT. In some particular cases noted herein, where the air gap is less than approximately 0.25 inches wide, the size of the air gap may not substantially affect the measurable depth of the MUT when the effective dielectric constant (k) of the MUT is greater than or equal to about four (4). However, where the MUT has a dielectric constant (k) less than approximately three (3), the air gap may have a significant effect on the measurable depth of the MUT. It is understood that air gaps smaller than approximately 0.25 inches wide may not have a significant impact on the measurable depth of the MUT even where the dielectric constant (k) of the MUT is less than approximately 3.

Figure 7:
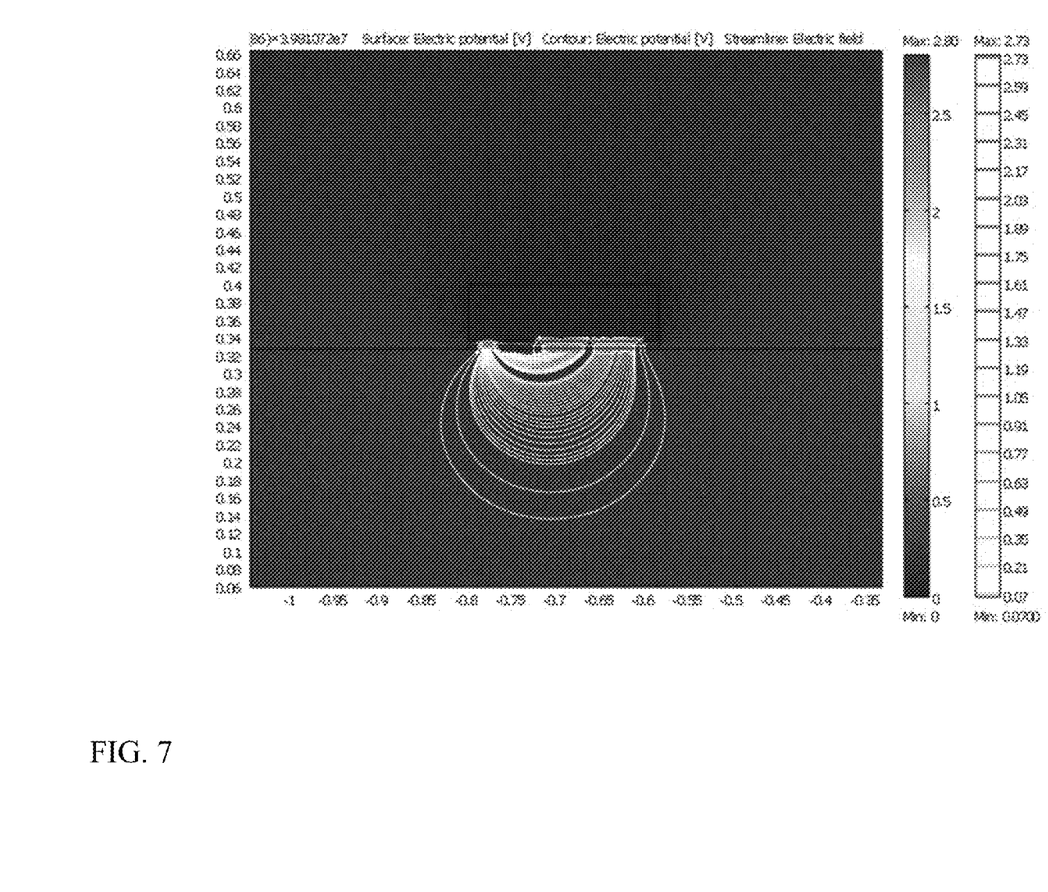
FIG. 7 shows a Comsol Multiphysics finite element model with a first electrode transmitting a signal and other electrodes receiving a return signal.
Figure 8:
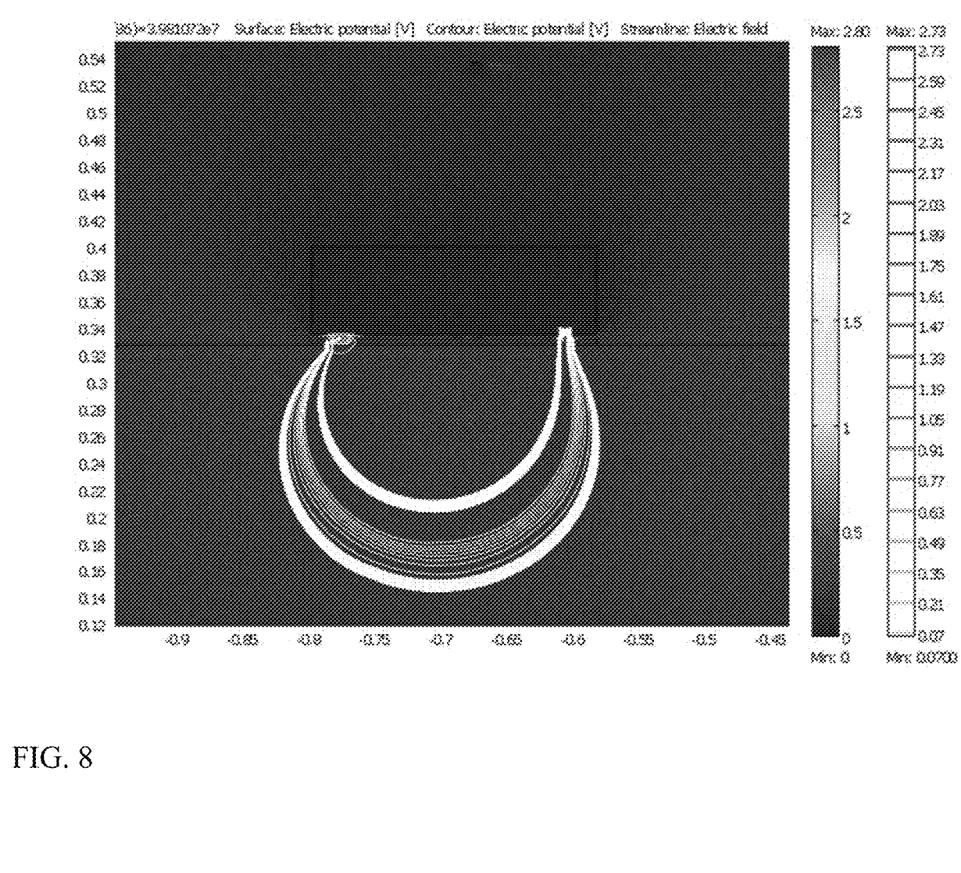
FIG. 8 shows a Comsol Multiphysics finite element model with a first electrode transmitting a signal and a single electrode receiving a return signal.

FIGS. 7 and 8 show field patterns of the sensor of FIGS. 5-6 using a field pattern program which can include any conventional finite element evaluation software program. FIG. 7 shows the field when E1 (FIGS. 5-6) is transmitting and all the other electrodes are receiving. FIG. 8 shows the fields when E1 (FIGS. 5-6) is transmitting and only E4 (FIGS. 5-6) is receiving. These computations were made using glass as the target material, but could apply to a number of other materials under test. The electromagnetic properties of the actual material under test can be used in the modeling. The Applicants have used this code successfully to design sensors for measurement of asphalt and soil properties and assessment of suitability for use in detection of buried mines.

However, one difference in this design when compared with Applicants' previous work is that this design is amenable for use in the tomographic application and the measurement of material properties in a number of different layers/volumes. The sensor design will also be compatible with product dimensions and electromagnetic properties.

Tomographic Methodology:

As noted above, there are many methods to develop tomographic representations from impedance data. Most of the approaches require that the impedance data be taken from a multidimensional array and provide a 3-D visualization of the target. One novel tomographic approach according to various embodiments of the invention is to use the linear (one dimension) array to provide a 2-D measurement of the impedance of the target at different layers/volumes.

This illustrative design disclosed according to embodiments herein is a four electrode array with each electrode capable of being either a transmitter or a receiver, as shown in FIG. 6. This permits three impedance measurements in Layer 1, C11, C12, and C13; and two in Layer 2, C21 and C22; and one in Layer 3, C31.

Figure 9:
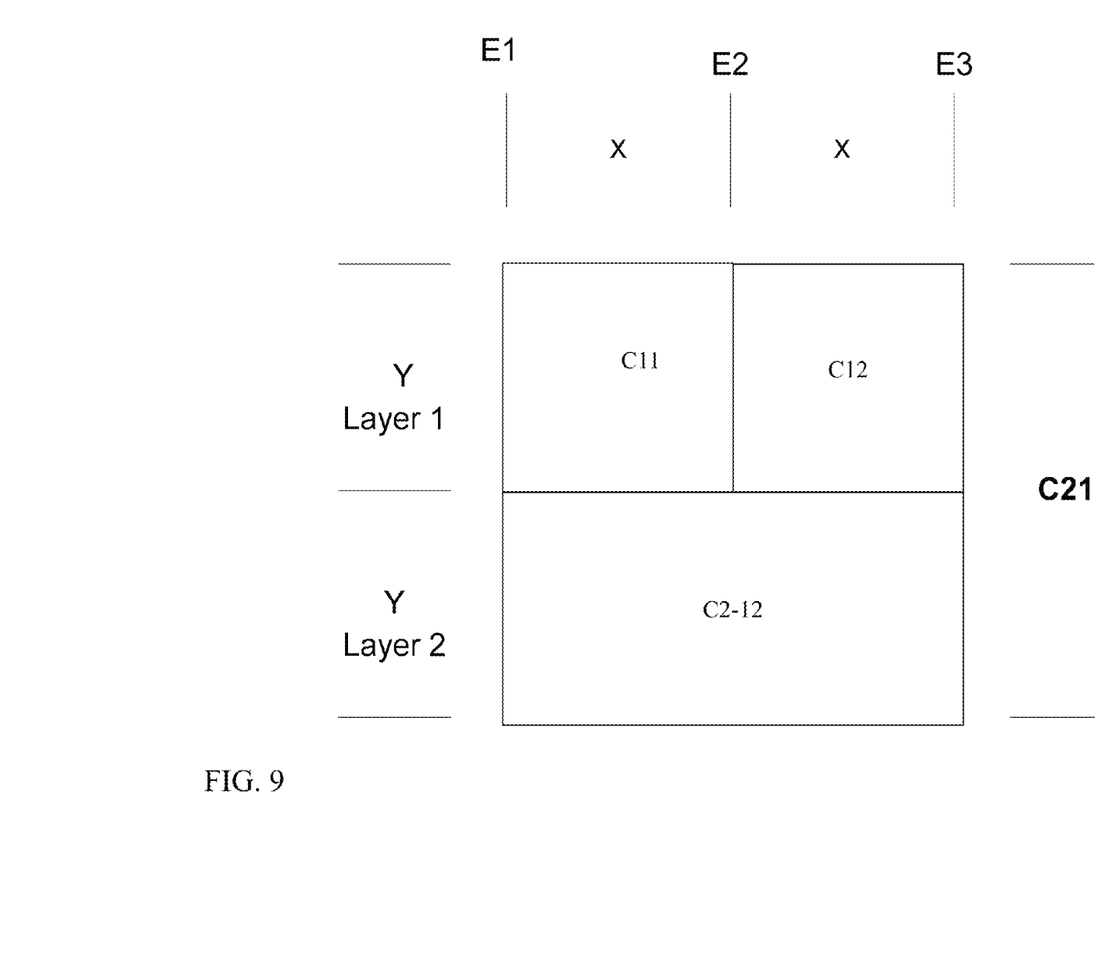
FIG. 9 is an illustration of the basic inversion model.

For Layers 1 and 2, the measured volumes can be considered as "voxels" as shown in FIG. 9; where C11, C12, and C21 are the measured volumes. Using the measured voxels in series and parallel with each other, an initial approach to determining the tomographic values of each layer is identified. The objective is to determine the electrical properties/characteristics of each level. Using the measurements of C11, C12 and C21, the calculation of the subsurface voxel in Level 2, e.g., C2-12, can be determined using circuit theory of impedances in series and parallel. The "total measurement", $Z_{C21}=(Z_{C11}+Z_{C12})\|Z_{C2-12}$, is represented in the first equation below and the transformation of this equation that can be used to solve for the unknown Layer 2 volume, $Z_{C2-12}$, as shown in the next equation:

$$Z_{C21} = \frac{(Z_{C11} + Z_{C12}) * Z_{C2-12}}{(Z_{C11} + Z_{C12}) + Z_{C2-12}} \quad \text{(Equation 8)}$$

$$Z_{C2-12} = \frac{(Z_{C11} + Z_{C12}) * Z_{C21}}{(Z_{C11} + Z_{C12}) - Z_{C21}} \quad \text{(Equation 7)}$$

An issue can be in defining the geometry factors since these equations assume that the spacing is equal in each direction. By constraining the planar linear array to equally spaced electrodes, thereby deliberately limiting the degrees of freedom, the equations will stand. However, this limits the design and application of the sensor and ignores the fact that that the measured volumes are not simple rectilinear volumes.

Example Application According to Various Embodiments

An industry that requires a system as presented in this application is the manufacture of concrete blocks used as pavers. The prior illustration and description is based upon the specification for this industry.

Concrete paver blocks can range in size from 4-inches width, 8-inches long and 4-inches thick to 24-inches square and 2.5-inches thick. The pavers are fabricated out of various mixes of concrete placed into a form to mold the desired shapes. These fresh blocks must meet specified moisture levels and density so that they will cure into a block with the desired strength characteristics. These blocks move out of the forming area on palates which are moved to curing areas where they are held for a period. The current quality check consists of removing a block from the production line and taking it to a measurement area. The block is weighed to determine its density based upon the design block dimensions. The block is then broken down and placed into an oven where it is dried. It is then weighed.

The difference between the dry weight and the wet weight is the weight of the water that was in the block. There is often a considerable time between the selection of the sample and the results of the test being available. During this time, production is continuing. If the block is out of specification, then all the blocks produced during the time it took to do the testing are probably also out of specification. This results in lost production and scrappage (discarding of finished products).

The systems (including sensor, computer program(s), computer systems, etc.) described according to the various embodiments of the invention are designed to readily measure blocks of different thicknesses and for the thicker blocks to measure up to three separate layers/volumes.

Figure 10:
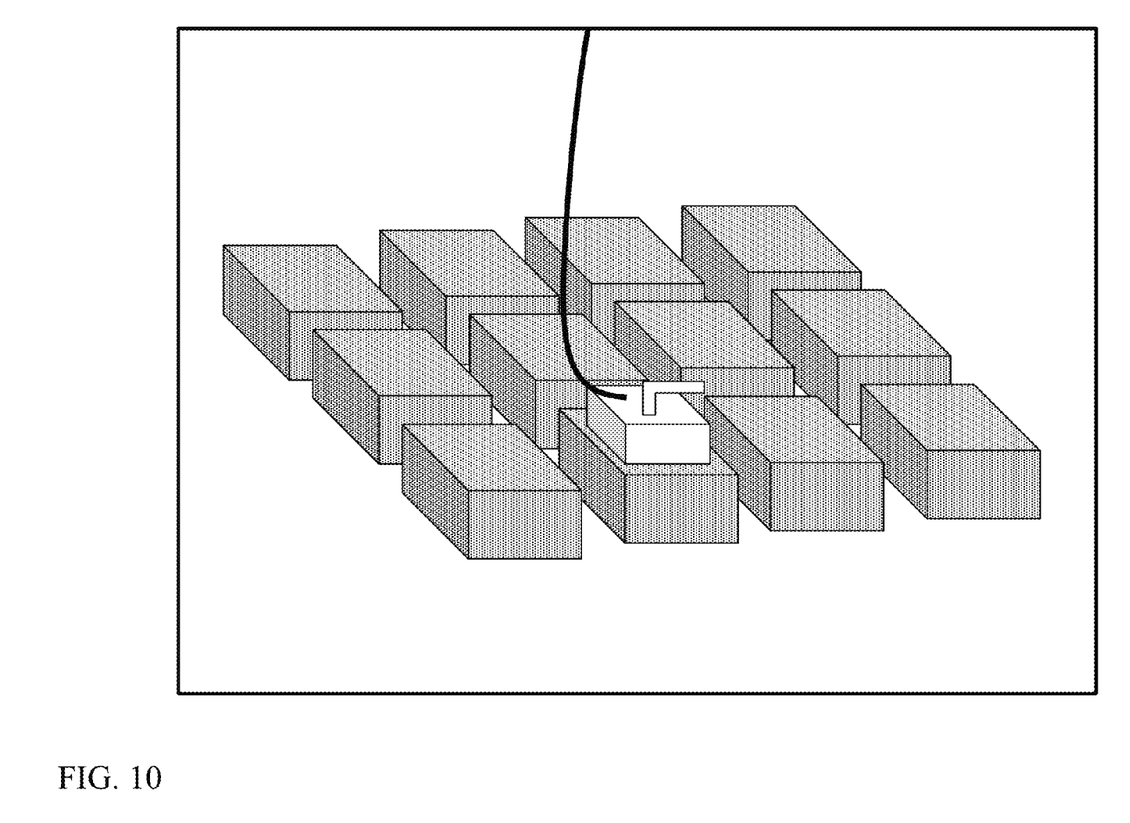
FIG. 10 is a conceptual drawing of an apparatus according to various embodiments of the invention.

The conceptual design of the system (including the sensor) in FIG. 10 is sized to fit on the smallest block in a batch. It is also designed to permit integration into an automatic testing fixture that might be able to perform 100% sampling of production.

The system is also capable of sampling the blocks in the curing area. The advantage is that if the curing is completed earlier than the fixed time, the overall production rate is increased.

For a 4-inch thick block, three layers can be measured as described above. The complex impedance values for the three layers/volumes of interest are determined by the various methods described herein. These values are used in an algorithm to relate the complex impedance spectra to the desired properties of the product.

The algorithm of the complex impedance may include the development of a function of the susceptance or conductance over a range of frequencies or an empirical correlation of the complex impedance to one or more physical properties of the material. This result can be transmitted either to display for manual data entry or to a statistical process control program. The manual evaluation is able to result in a pass-fail result or the data may be entered into some type of statistical analysis for further processing and evaluation. A statistical process control program determines if the sample meets the required quality within a specified statistical limit. Whichever method is used, the result is then passed to the manufacturing process control for action.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. It is further understood that the terms "front" and "back" are not intended to be limiting and are intended to be interchangeable where appropriate.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A system comprising:
   an array of electrodes for non-conductively communicating with a material under test (MUT);
   a signal generator operably connected with the array of electrodes, the signal generator for transmitting oscillating electromagnetic field signals from the array of electrodes at a range of frequencies; and
   at least one computing device operably connected with the signal generator and the array of electrodes, the at least one computing device configured to:
   obtain a return signal from the array of electrodes about the MUT;
   compare the return signal with the oscillating electromagnetic field signals to determine a difference in an aspect of the return signal and the aspect of the oscillating electromagnetic field signals;
   compare the difference in the aspect to a predetermined threshold; and
   determine a characteristic of the MUT based upon the compared difference in the aspect and the predetermined threshold, wherein the compared difference in the aspect of the return signal and the aspect of the transmitted oscillating electromagnetic field signals represents a complex impedance of the MUT, and wherein the characteristic of the MUT is determined using an algorithm including a function of a susceptance or conductance of the MUT over the range of frequencies, or an empirical correlation of the complex impedance to one or more physical properties of the MUT.

2. The system of claim 1, wherein the array of electrodes includes at least one transmitting electrode and at least one sensing electrode.

3. The system of claim 1, wherein the array of electrodes includes a two-dimensional planar array.

4. The system of claim 1, wherein the oscillating electromagnetic field signals are transmitted into the MUT over the range of frequencies.

5. The system of claim 1, wherein the comparing of the aspect of the return signal with the aspect of the oscillating electromagnetic field signals includes comparing the aspect of the return signal with the aspect of the oscillating electromagnetic field signal across a complex impedance spectrum.

6. The system of claim 5, wherein the aspect of the return signal includes at least one of a magnitude or a phase of the return signal and the aspect of the oscillating electromagnetic field signals include a corresponding one of the at least one of the magnitude or the phase of the oscillating electromagnetic field signals.

7. The system of claim 1, wherein the array of electrodes includes at least three electrodes, and wherein each of the at least three electrodes is configured to transmit and receive the electromagnetic signal.

8. A computer program comprising program code stored on a non-transitory computer-readable medium, which when executed by at least one computing device, causes the at least one computing device to:
provide instructions for transmitting oscillating electromagnetic field signals to a material under test (MUT);
obtain a return signal associated with the transmitted oscillating electromagnetic field signals;
compare the return signal with the oscillating electromagnetic field signals to determine a difference in an aspect of the return signal and the aspect of the oscillating electromagnetic field signals;
compare the difference in the aspect to a predetermined threshold; and
determine a characteristic of the MUT based upon the compared difference in the aspect and the predetermined threshold, wherein the compared difference in the aspect of the return signal and the aspect of the transmitted oscillating electromagnetic field signals represents a complex impedance of the MUT, and wherein the characteristic of the MUT is determined using an algorithm including a function of a susceptance or conductance of the MUT over the range of frequencies, or an empirical correlation of the complex impedance to one or more physical properties of the MUT.

9. The computer program of claim 8, wherein the providing includes providing the instructions to a signal generator operably connected with an array of electrodes, the signal generator for transmitting the oscillating electromagnetic field signals from the array of electrodes at the range of frequencies.

10. The computer program of claim 8, wherein the aspect of the return signal includes at least one of a magnitude or a phase of the return signal, and the aspect of the oscillating electromagnetic field signals include a corresponding one of the at least one of the magnitude or the phase of the oscillating electromagnetic field signals.

11. A computer-implemented method comprising:
providing instructions for transmitting oscillating electromagnetic field signals to a material under test (MUT);
obtaining a return signal associated with the transmitted oscillating electromagnetic field signals;
comparing the return signal with the oscillating electromagnetic field signals to determine a difference in an aspect of the return signal and the aspect of the oscillating electromagnetic field signals;
comparing the difference in the aspect to a predetermined threshold; and
determining a characteristic of the MUT based upon the compared difference in the aspect and the predetermined threshold, wherein the compared difference in the aspect of the return signal and the aspect of the transmitted oscillating electromagnetic field signals represents a complex impedance of the MUT, and wherein the characteristic of the MUT is determined using an algorithm including a function of a susceptance or conductance of the MUT over the range of frequencies, or an empirical correlation of the complex impedance to one or more physical properties of the MUT.

12. The method of claim 11, wherein the providing includes providing the instructions to a signal generator operably connected with an array of electrodes, the signal generator for transmitting the oscillating electromagnetic field signals from the array of electrodes at the range of frequencies.

13. The method program of claim 11, wherein the array of electrodes is electrically isolated from the MUT.

14. The method of claim 11, wherein the oscillating electromagnetic field signals are transmitted into the MUT at the range of frequencies.

15. The method of claim 11, wherein the aspect of the return signal includes at least one of a magnitude or a phase of the return signal, and the aspect of the oscillating electromagnetic field signals include a corresponding one of the at least one of the magnitude or the phase of the oscillating electromagnetic field signals.

* * * * *